(12) United States Patent
Ogilvie

(10) Patent No.: US 6,217,616 B1
(45) Date of Patent: Apr. 17, 2001

(54) ELBOW PROSTHESIS

(75) Inventor: William F. Ogilvie, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 0 days.

(21) Appl. No.: 09/387,411

(22) Filed: Aug. 31, 1999

Related U.S. Application Data

(60) Provisional application No. 60/099,659, filed on Sep. 9, 1998.

(51) Int. Cl.$^7$ .................................................. A61F 2/38
(52) U.S. Cl. ............................................... 623/20.11
(58) Field of Search .................. 623/20, 20.11, 623/20.12, 20.13

(56) References Cited

U.S. PATENT DOCUMENTS

| | | | |
|---|---|---|---|
| 3,879,767 | * 4/1975 | Stubstad | 623/21.19 |
| 3,990,117 | 11/1976 | Pritchard et al. . | |
| 4,194,250 | * 3/1980 | Walker | 623/23.39 |
| 4,199,824 | * 4/1980 | Nieder | 623/23.29 |
| 4,242,758 | 1/1981 | Amis et al. . | |
| 4,293,963 | 10/1981 | Gold et al. . | |
| 4,332,037 | * 6/1982 | Esformes et al. | 623/18.12 |
| 4,378,607 | 4/1983 | Wadsworth et al. . | |
| 4,383,337 | 5/1983 | Volz et al. . | |
| 4,538,306 | 9/1985 | Dörre et al. . | |
| 4,936,854 | 6/1990 | Swanson . | |
| 5,030,237 | 7/1991 | Sorbie et al. . | |
| 5,782,922 | * 7/1998 | Vandewalle | 623/20.11 |
| 5,782,923 | 7/1998 | Engelbrecht et al. . | |
| 5,879,395 | 3/1999 | Tornier et al. | 623/20 |

FOREIGN PATENT DOCUMENTS

| | | | |
|---|---|---|---|
| 4331282 | 3/1995 | (DE) . | |
| 132284 | * 1/1985 | (EP) | 623/20 |
| 0607749 | 7/1994 | (EP) . | |
| 2663838 | 1/1992 | (FR) . | |
| 2094639 | * 9/1982 | (GB) | 623/20 |
| 1537479 | 6/1990 | (GB) . | |
| 1734727 | 5/1992 | (SU) . | |

OTHER PUBLICATIONS

Cook, et al., "Wear Characteristics of the Canine Acetabulum Against Different Femoral Prostheses", *1989 British Editorial Society of Bone and Joint Surgery*, vol. 71–B, No. 2, Mar. 1998, pp. 189–197.

Worsing, Jr. et al., "Reactive Synovitis from Particulate Silastic", *The Journal of Bone and Joint Surgery, Inc.*, vol. 64–A, No. 4, Apr. 1982, pp. 581–585.

(List continued on next page.)

*Primary Examiner*—Gene Mancene
*Assistant Examiner*—Eduardo C. Robert
(74) *Attorney, Agent, or Firm*—Fitch, Even, Tabin & Flannery

(57) ABSTRACT

Asymmetric and axisymmetric prostheses for replacement of the radial head are shown which are designed to smoothly interengage with the annular ligament of the radius and effectively allow a patient to recover normal functioning of the forearm. These prostheses have head, collar and stem sections, and the undersurface of the head which surrounds the collar provides a shoulder which is excellently gripped by the annular ligament through which the prosthesis is inserted during implantation, assuring achievement of the desired juxtaposition between the periphery of the prosthesis head and the radial notch of the ulna. In the asymmetric embodiment, shaping the head to provide a proximal surface of generally oval cross-section having an offset concave surface and a medial region of greater thickness offers particular advantages.

12 Claims, 3 Drawing Sheets

OTHER PUBLICATIONS

Bohl, et al., "Fracture of a Silastic Radial–Head Prosthesis: Diagnosis and Localization of Fragments by Xerography", *The Journal of Bone and Joint Surgery, Inc.*, vol. 63–A, No. 9, Dec. 1981, pp. 1482–1483.

Pribyl, et al., "The Effect of the Radial Head and Prosthetic Radial Head Replacement on Resisting Valgus Stress at the Elbow", *Orthopedics*, 1986, pp. 723–726.

Knight, et al.; "Primary Replacement of the Fractured Radial Head with a Metal Prosthesis", *The Journal of Bone and Joint Surgery, Inc.*, vol. 75–B, No. 4, Jul. 1993, pp. 572–576.

Carn, et al., Silicone Rubber Replacement of the Severely Fractured Radial Head, *Clinical Orthopedics and Related Research*, No. 209, Aug. 1986, pp. 259–269.

Hotchkiss, "Displaced Fractures of the Radial Head: Internal Fixation or Excision?", *Journal of the American Academx of Orthopaedic Surgeons*, vol. 5, No. 1, Jan./Feb. 1997, pp. 1–10.

* cited by examiner

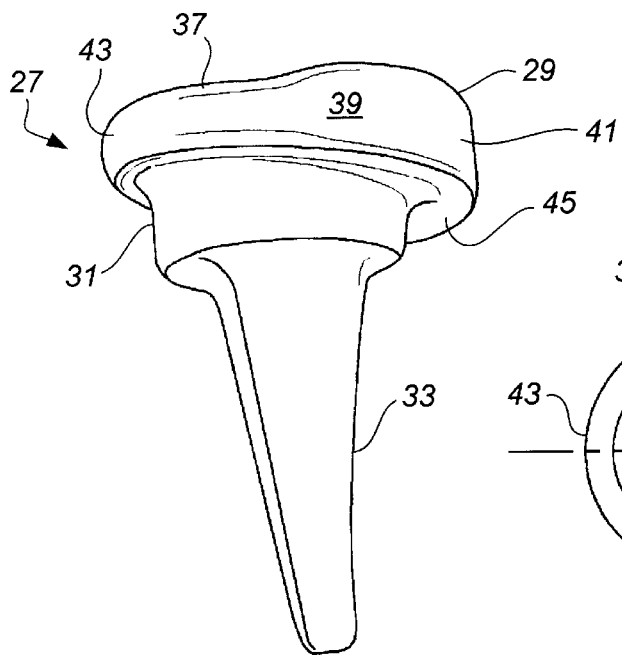
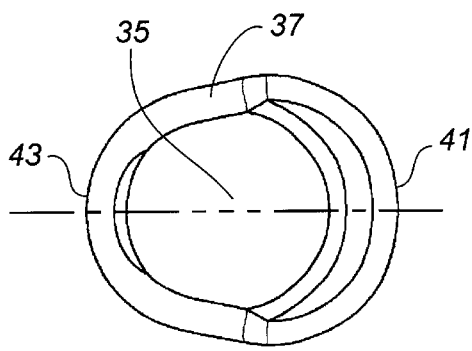
FIGURE 5  FIGURE 6
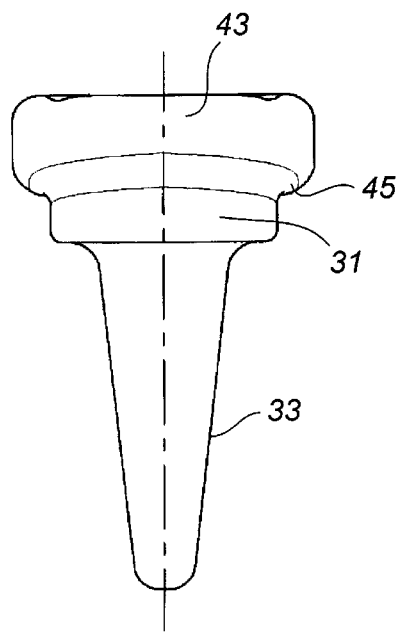
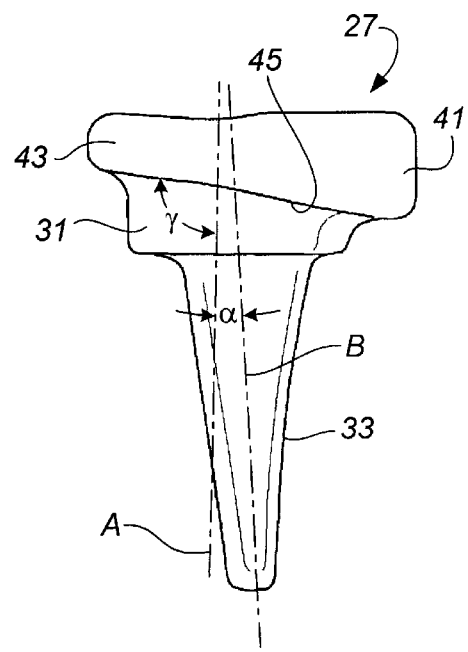
FIGURE 7  FIGURE 8

ELBOW PROSTHESIS

This application claims priority from U.S. provisional application Ser. No. 60/099,659, filed Sep. 9, 1998.

This invention relates to an elbow prosthesis and more particularly to a prosthesis for replacing the end portion of the radius.

BACKGROUND OF THE INVENTION

Fractures of the radial head constitute one of the two most common fractures of the elbow, and treatment of radial head fractures has been a controversial subject. Although excision of the head of the radius can sometimes give good long-term results, such may often cause persistent elbow or wrist pain associated with cubitus valgus or with proximal radial migration. As a result, prosthetic replacements have been frequently recommended to obviate these problems and to improve stability of the elbow joint.

Radial heads have sometimes been replaced with flexible silicone rubber prostheses, particularly in cases of severe rheumatoid arthritis and degenerative arthritis, and such replacements have been suggested for comminuted fractures of the radial head. However, because a silicone rubber radial head is quite flexible, compared to bone, the ability of such a flexible implant to transfer dynamic forces across the radial-capitellar joint without excessive deformation is questioned. Clinical and biomechanical studies have now indicated that replacement of a radial head with a prosthesis made of silicone rubber, which is much less stiff than bone and deforms under load, does not reestablish the true mechanical function of the natural radial head because such a silicone rubber prosthesis may be unable to transmit physiological forces from the proximal radius to the capitellum; this indicates that a less flexible radial head prosthesis should result in more normal physiologic stress transfers and provide improved clinical results. Moreover, fractures of silicone rubber devices have also been reported.

Both metal and acrylic radial head replacements have now been clinically implanted. Although there is only limited experience with prostheses made of metal, the elastic moduli of certain metals, such as titanium, can be as much as 10 times greater than the elastic modulus of bone, and this very substantial difference often results in a biomechanical incompatibility between the bone of the capitulum and the radial head replacement prosthesis. Moreover, the difference has also been such as to cause undesirable changes in cartilage in situations where there is cartilage at the wear surface.

Shown in U.S. Pat. No. 5,782,923 is one endoprosthesis for replacing the entire elbow joint wherein a radius component is mounted in the bone by a shaft portion and has a spherical head that is received in a recess of a member that slides in a socket formed in the undersurface of a flange portion of the ulnar component. U.S. Pat. No. 5,030,237 shows an elbow prosthesis which includes a humeral insert made of a metal alloy, such as Vitallium, and an ulna prosthesis, wherein the end of the radius may be optionally replaced.

Although the results of certain metal and polymeric implants have been promising in some aspects, none of these replacements have been totally satisfactory. Accordingly, the search has continued for more satisfactory radial head replacements that better mimic the properties of the natural radius head.

SUMMARY OF THE PRESENT INVENTION

In accordance with one aspect of the present invention, an improved prosthesis for the replacement of the end portion or head of the radius is provided which includes a body having a head, a collar and a stem with the stem being proportioned to be received within the medullary cavity of the radius. The head is shaped so as to smoothly interface with the capitulum of the humerus, having a peripheral surface which extends completely about the head, an undersurface and a concave proximal end surface for contact with the capitulum. This concave surface is surrounded by a rim, and in one aspect, the peripheral surface varies in height with the medial region extending further in a distal direction than the lateral region so that the medial region of the head is substantially thicker. In another aspect, the prosthesis is designed to be axisymmetric so that height of the peripheral surface is uniform. The collar is located between the undersurface of the head and the stem, and in one aspect, it is aligned at an oblique angle to the axis of rotation of the radius in pronation-supination movement.

In these various embodiments, the collar has a lesser cross-sectional dimension than the head; thus, the undersurface of the head circumscribes the collar and provides a peripheral shoulder against which the annular ligament of the elbow, in which the collar portion of the head resides, may articulate. The undersurface is preferably substantially planar and, in one aspect, is aligned at an angle of between about 95° and about 105° to the axis of rotation of the radius in pronationsupination movement.

In one particular aspect of the invention, the concave surface in the end of the prosthesis is not centered; instead, it is offset from the center of the head in a direction toward the lateral region. Moreover, viewing the prosthesis looking toward the proximal end surface, a cross-sectional shape is seen, which is generally ovoid, with the medial region of the head being wider in the interior-posterior plane than is the lateral region, preferably with the medial region of the peripheral surface having a radius of curvature at least about 15% greater than that of the lateral region. In such construction, the centerline of the stem that is received within the medullary cavity is preferably aligned at an angle of between about 8° and about 22° to the axis of rotation of the radius in pronationsupination movement.

BRIEF DESCRIPTION OF THE DRAWINGS

FIG. 5 is a perspective view of the prosthesis of FIG. 3 taken from a different angle.

FIG. 6 is a top view of the prosthesis of FIG. 3.

FIG. 7 is a left side elevation view of the prosthesis of FIG. 3.

FIG. 8 is a front elevation view of the prosthesis of FIG. 3.

DETAILED DESCRIPTION OF THE PREFERRED EMBODIMENTS

Figure 1:
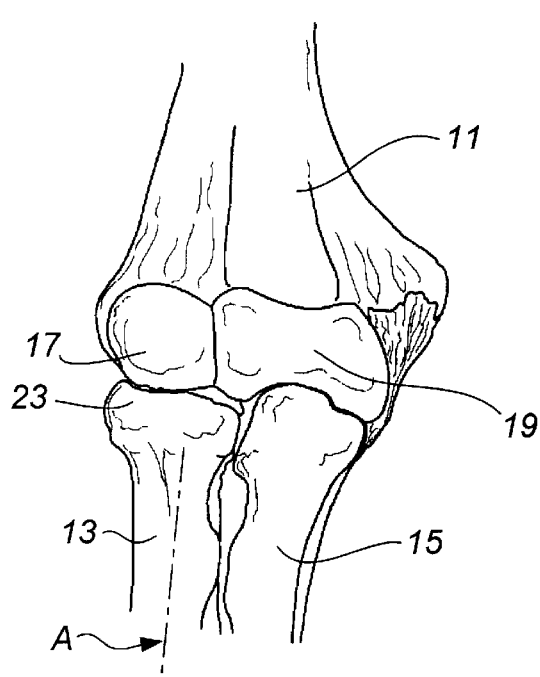
FIG. 1 is a fragmentary view showing the three bones of the human elbow.

Illustrated in FIG. 1 is the distal end portion of the humerus 11 along with the proximal end portions of the radius 13 and the ulna 15. The distal end portion of the humerus includes a portion referred to as the capitulum 17 against which the radius articulates and a portion referred to as the trochlea 19 against which the ulna articulates. The radius 13 is located on the thumb side of the forearm. The ulna 15 forms a hinge joint with the humerus 11 which allows for flexion and extension of the forearm. The capitulum 17 is located on the lateral side of the humerus and has a convex, generally spherical shape. The ulna includes a trochlear notch 21 which extends in a proximal direction and resides on the posterior of the distal end of the humerus 11. In contrast, a head 23 of the radius contacts only the capitulum 17 of the humerus and a radial notch 25 which is formed in the medial portion of the ulna 15.

The head 23 of the radius accordingly provides both an articular function and a load-bearing function. During elbow articulation, the concave surface slides on the capitulum during flexion and extension of the elbow and generally rotates on the capitulum during pronation and supination of the forearm and hand. In its loadbearing function, the contact with the capitulum 17 resists valgus forces applied to the arm and resists axial loads transmitted from the wrist to the elbow resulting from the gripping function of the hand.

Figure 2:
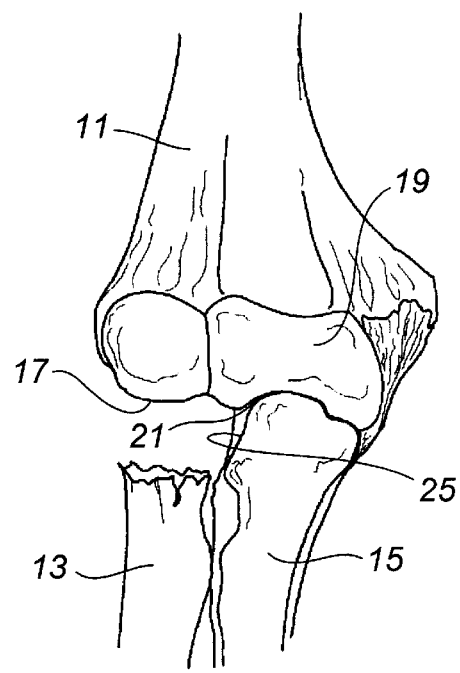
FIG. 2 is a view similar to FIG. 1 where the head of the radius has fractured and been removed.
Figure 3:
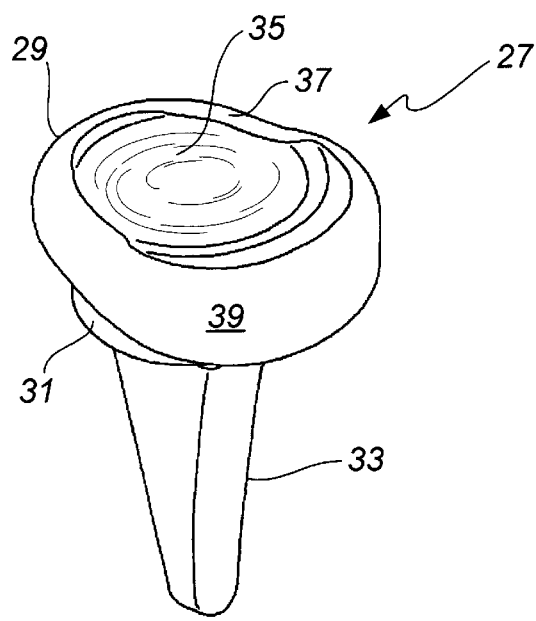
FIG. 3 is a perspective view of an asymmetric radial head replacement embodying various features of the present invention.
Figure 4:
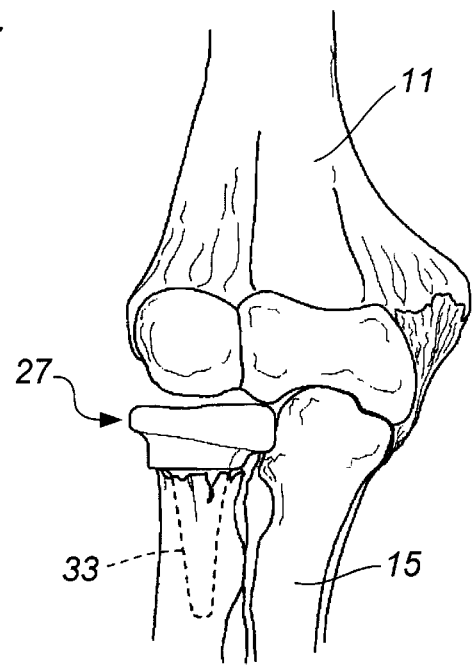
FIG. 4 is a fragmentary view of an elbow, similar to FIG. 2, showing the excised radius having been replaced with the prosthesis of FIG. 3, with spacing provided for clarity of explanation.
Figure 10:
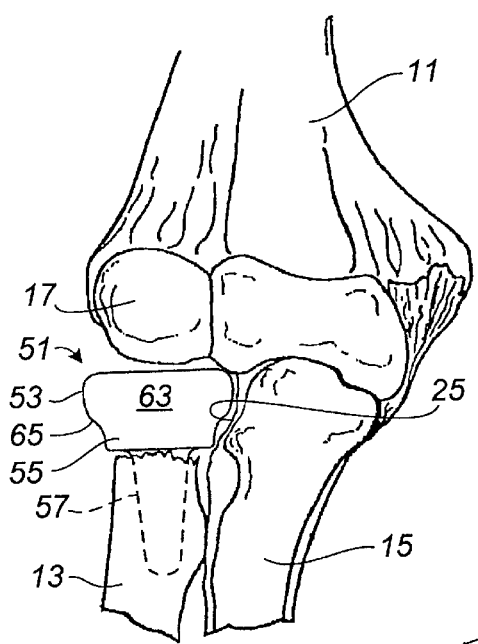
FIG. 10 is a view similar to FIG. 4 showing the prosthesis of FIG. 9 in elevation where it is replacing an excised end of the radius, with portions of the elbow removed and spaced apart for clarity.
Figure 9:
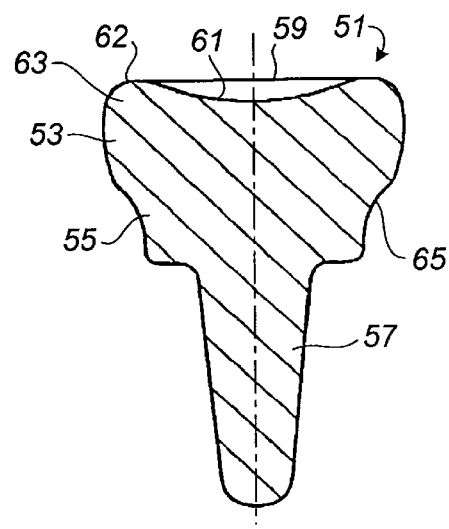
FIG. 9 is a sectional view of a axisymmetric radial head prosthesis embodying various features of the present invention and having some similarity to that shown in FIGS. 3–8.

When it is necessary to replace the proximal head 23 of the radius for any reason, an asymmetric prosthesis 27 as illustrated in FIG. 3 may be used to replace it; an alternative axisymmetric prosthesis is shown in FIGS. 9 and 10. FIG. 2 shows an elbow joint with the head of the radius excised, and FIG. 4 shows that joint wherein the head of the radius 13 has been replaced with the prosthesis 27. During pronation-supination of the forearm, the radius rotates about an axis which is generally defined by the proximal head of the radius and the distal head of the ulna.

The prosthesis 27 has a head 29, a collar 31 and a stem 33, with the stem portion of the prosthesis being proportioned to be received with the medullary cavity of the radius. The stem 33 is generally polygonal in cross-section so as to resist any rotation relative to the radius 13 once implantation has taken place. The radial axis is defined as the axis which passes through the proximal and distal radial heads and is marked with the reference A in FIG. 1; the axis of the stem is marked with the reference B in FIG. 8. The stem axis passes through the center of capitulum 17 of the humerus but is not parallel to the radial axis, and the included angle between the stem axis and the radial axis is preferably between about 5° and about 22° (see angle a in FIG. 8).

The head portion 29 of the prosthesis has a proximal concave surface 35 which is shaped for contact with the capitulum 17. This concave surface 35 is surrounded by a peripheral rim 37, which lies at the proximal end of a peripheral surface 39 of the head, which surface extends completely therearound and varies in height as a result of the shape of the head. The head 29 is thicker in its medial region 41 than in its lateral region 43; thus, the peripheral surface 39 has a greater height in the medial region than in the lateral region. It is the medial volar-to-dorsal portion 41 of the peripheral surface which contacts the radial notch 25 of the ulna during rotation of the radius 13 about the radial axis. Thus, the alignment of the head 29 of the prosthesis in its implanted position is such that this surface portion 41 is generally parallel to the radial axis A. The proximal concave spherical surface 35 of the prosthesis which contacts the capitulum is axisymmetric about the radial axis; however, the periphery of the head 29 is not.

The centerline of the stem 33 of the prosthesis is offset from the radial axis at a slight angle to the medial side; however, there is a complementary orientation of the concave generally spherical surface 35 in the proximal face of the radius head. Thus, the concave, generally spherical surface 35 of the head 29 is axisymmetric with respect to the radial axis. A radius drawn between the center of such a sphere (the surface section of the capitulum) and the point on such sphere where the radial axis intersects forms the acute angle a (as previously mentioned) with a radius drawn to the point of intersection of the stem axis and such sphere, and such angle is preferably an angle between about 8° and about 10°.

The radius of curvature of the generally spherical concave surface 35 is matched so as to approximate the radius of curvature of the capitulum 17. As can best be seen from FIGS. 3 and 6, the concave surface 35 is not centered on the proximal end face of the prosthesis but is offset from a central location in a direction toward the lateral region 43. The distance from the center of the concave generally spherical surface 35 to the furthest point on the medial articular surface 41 is preferably between about 1.05 and about 1.2 times the distance to the furthest point on the periphery of the lateral section 43 of the head.

As can also be seen from FIG. 6, the medial region 41 of the head is wider in the anterior-posterior plane than is the lateral region 43; this creates a head, the cross-section of which is generally oval. Preferably, the radius of curvature of the medial portion 41 of the peripheral surface 39 is at least about 15% greater than the radius of curvature of the lateral portion 43 of the peripheral surface. This greater radius of curvature, coupled with the greater height of the peripheral surface in this region, provides for improved articulation of the head of the prosthesis with the radial notch 25 of the ulna 15. Medial portion 41 of the periphery of the head has a generally constant radius throughout the arc which will be in contact with the radial notch 25 of the ulna; this allows the radius 13 to rotate from supination to pronation and back while the concave, generally spherical articular surface 35 stays in contact with the capitulum 17. As a result of this constant radius, the axial center of rotation of the radius 13 passes through the center of the generally spherical section of the capitulum 17, regardless of whether the elbow is in flexion or extension.

The head 29 has an undersurface 45 that is substantially planar and provides a peripheral shoulder against which the annular ligament of the elbow may articulate. As best seen in FIG. 8, the undersurface in the prosthesis 27 is aligned at an angle of greater than 90° to the axis of rotation A of the radius, and preferably, this angle γ is between about 95° and about 105°. The annular ligament is generally ring-shaped, and functions in combination with the collateral ligament. The stem 33 of the prosthesis 27 is passed through the center of the annular ligament when the replacement prosthesis is installed so that, in its operative location, the annular ligament circumscribes the collar region 31 of the prosthesis. The collar 31 is proportioned to fit within the annular ligament and has an appropriate cross-sectional shape; it is preferably elliptical, oval or circular, and more preferably has an oval cross-section. The reduced height of the lateral section 43 of the periphery can be advantageous in providing clearance for the annular ligament, and such can result in an extremely compatible fit. Moreover, because of the thinner lateral portion of the periphery, this clearance also allows the collateral ligament to better apply reducing force to the joint by supporting the lateral side of the annular ligament that is juxtaposed therewith. This arrangement has been found to provide excellent stability and to facilitate exceptionally smooth rotational movement of the radius.

The surface of the medial portion 41 of the periphery of the head articulates with the depression in the side of the ulna 15 referred to as the radial notch 25 and forms what is referred to as the proximal radioulnar joint. When the forearm is moved in flexion/extension motion, the radial head 29 slides on the capitulum 17 moving generally about a surface that essentially defines the axis of rotation of the ulnar. However, when the forearm is moved in pronation—supination movement, the radial head 29 rotates on the capitulum 17 about the axis of rotation of the radius, while sliding slightly because of the axisymmetric orientation of the concave surface 35.

Illustrated in FIG. 9 is an alternative embodiment of a prosthesis for replacement of the radial head which is formed so as to be axisymmetric, which is advantageous in that the surgeon making the implantation need not be concerned with obtaining precise angular orientation of the implanted prosthesis. An axisymmetric prosthesis 51 is shown which has a head 53, a collar 55 and a stem 57. The stem is proportioned to be received within the medullary cavity of the radius, and although it may be circular in cross-section in order to be truly axisymmetric, it may alternatively have the cross-section of a regular polygon with rounded edges. The prosthesis 51 is symmetric about the vertical axis shown in FIG. 9, as a result of which both the head 53 and the collar 55 are circular in cross-section. The proximal surface 59 of the prosthesis 51 has formed within it a shallow concave surface 61 which in this embodiment is located symmetrically about the vertical centerline. The concave surface 61, as was the previously described concave surface 35, is shaped for surface contact with the capitulum 17 and is surrounded by a rim portion 62.

The peripheral surface of the head is marked with the reference numeral 63 and, in this axisymmetric prosthesis, is of uniform height and is oriented generally parallel to the vertical axis as seen in FIG. 9. The peripheral surface terminates in an undersurface in the form of an annular shoulder 65 which surrounds the collar 55 and which is generally transverse to the peripheral surface 63. As in the case of the prosthesis 27, the peripheral surface contacts the radial notch 25 of the ulna 15 during rotation of the radius 13 about its radial axis. The radius of curvature of the peripheral surface 63 is accordingly generally matched to that of the radial notch 25, and it is preferably between about 5% and 20% less than the curvature of the radial notch. This of course determines the diameter of the head 53.

The shoulder 65 in combination with the cylindrical collar 55 again provides an annular surface region against which the annular ligament of the elbow articulates, and the spacing between the surface of the collar 55 and the periphery 63 of the head is controlled so as to render this shoulder region most effective for this purpose. In this respect, the diameter of the collar 55 should be equal to between about 60% and about 75% of the diameter of the head 153 and preferably is at least about 65% thereof. The axial height of the collar should be a fraction of its own diameter, e.g. about 20% to 40% thereof, and preferably at least about 30% thereof. Preferably, the axial height of the collar 55 is equal to between about 35% and 45% of the total height of the head 53 plus the collar 55. As in the case of the head 29, the peripheral surface 63 which contacts the radial notch has a radius of curvature that is between about 5% and about 20% less than the curvature thereof, and the radius of curvature of the collar 55 is preferably at least about 15% less than that of the periphery of the head, and more preferably about 70 to about 80% thereof.

Figure 12:
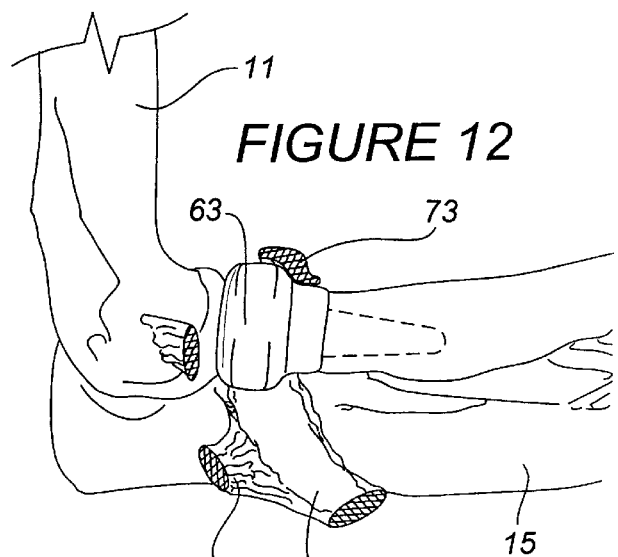
FIG. 12 is a view similar to FIG. 11 with the ligaments shown as being partially severed and peeled away from the radius for purposes of illustration.
Figure 11:
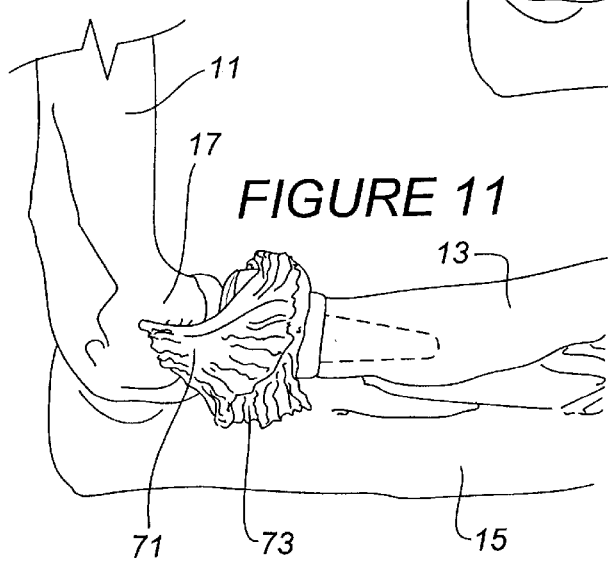
FIG. 11 is a view of the elbow shown in FIG. 10 with the forearm bent at 90° which shows both the radial collateral ligament and the annular ligament of the radius.

The prosthesis 51 is illustrated in FIGS. 10–12 following being implanted in a radius 13 having its natural head removed. These figures illustrate the cooperation between the radial collateral ligament 71 and the annular ligament 73 of the radius. FIG. 11 shows the interaction between the two ligaments. FIG. 12 illustrates the ligaments as being severed and peeled back to better show their interaction with the prosthesis 51. This view accentuates the attachment of the radial collateral ligament 71 to the humerus 11 and shows how it is juxtaposed in supporting fashion about the annular ligament 73 of the radius within which the head 53 is located. These views also better demonstrate how the positioning of the shoulder 65 and the collar 55 provides an annular region which can be excellently gripped by the annular ligament 73 so that the patient will regain normal functioning of the forearm following replacement of the proximal end of the radius 13.

It should also be seen from these views, FIGS. 10–12, that, during rotation, the radial head 29 of the prostheses is held against the radial notch 25 by means of the strong annular ligament 73 which is attached to the ulna 15 and which is supported by the collateral ligament 71 that is in turn attached to the humerus 11, extending from a lateral region of the capitulum 17, about the head and over the annular ligament 73. The annular region provided by the shoulder and the collar provides for excellent capture of the head by the radial collateral ligament and articulation therewithin, and in the asymmetric prosthesis 27, the annular orientation of the undersurface 45 further promotes this desirable interaction.

It has been found that pyrolytic carbon-coated graphite substrates can be used to create prostheses having a modulus of elasticity within about 150% of the modulus of elasticity of natural bone; thus, this is considered to be a preferred material for manufacturing such prostheses. Moreover, a new type of pyrocarbon that has been developed, which is being marketed as On-X carbon (see U.S. Pat. No. 5,641, 324), has particularly advantageous properties for use in orthopedic prostheses such as these, particularly when such is coated upon a substrate of isotropic fine grain graphite. Such results in the creation of a strong radial head prosthesis which has excellent biomechanical properties. Because pyrocarbon is both physiologically inert and biochemically compatible with bone, and because the elastic modulus of such a pyrocarbon-coated graphite substrate is very close to that of cortical bone, such a prosthesis is highly biomechanically compatible and may be effectively implanted without bone cement. As a result, bone tissue will grow into intimate contact with the stem of the implant, promoting osseous integration of the stem into the bone of the radius. In addition to its highly compatible modulus of elasticity, pyrocarbon, and particularly On-X carbon, illustrates excellent wear characteristics at its interface with bone and also with cartilage, resulting in an implant which is highly compatible.

Although the invention has been described with respect to certain preferred embodiments which constitute the best mode currently known for constructing the invention, it should be understood that various changes and modifications may be made without departing from the scope of the invention which is set forth in the claims appended hereto.

Particular features of the invention are emphasized in the claims which follow.

What is claimed is:

1. An elbow prosthesis for insertion into a human elbow to replace the end portion of the radius, which prosthesis comprises a body having a head, a collar and a stem, said stem being proportioned to be received within the medullary cavity of the radius, said head being shaped so as to smoothly interface with the capitulum of the humerus, and said head having a peripheral surface which extends completely about said head, an undersurface and a concave proximal surface for contact with the capitulum, which concave surface is surrounded by a rim, a medial region of said head extending further in a distal direction than does a lateral region thereof so that said medial region of said head is substantially thicker than said lateral region of said head and said peripheral surface has a greater height in said medial region than in said lateral region, said collar being located between said undersurface and said stem and being aligned at an angle to the axis of rotation of the radius in pronation-supination movement, and said collar being lesser in cross-sectional dimension than said head so that said undersurface of said head circumscribes said collar providing a peripheral shoulder.

2. The elbow prosthesis of claim 1 wherein said undersurface is substantially planar and is aligned at an angle between about 95° and about 105° to said axis of rotation of said radius and provides said peripheral shoulder against which the annular ligament of the elbow may articulate.

3. The elbow prosthesis of claim 2 wherein said concave surface is offset from a central location in said proximal surface of said head in a direction toward said lateral region.

4. The elbow prosthesis of claim 1 wherein said medial region of said head is wider in the anterior-posterior plane than is said lateral region so that said peripheral surface has a cross section which is generally ovoid.

5. The elbow prosthesis of claim 4 wherein said medial region of said peripheral surface has a radius of curvature at least about 15% greater than that of said lateral region thereof.

6. The elbow prosthesis of claim 1 wherein the centerline of said stem is aligned at an angle of between about 8° and about 22° to said axis of rotation of said radius.

7. An elbow prosthesis for insertion into a human elbow to replace the end portion of the radius and to interengage with the capitulum of the humerus and the radial notch of the ulna, which prosthesis comprises a one-piece body having an integral head, collar and stem, said stem being of polygonal cross-section and being proportioned to be received within the medullary cavity of the radius, said head being shaped so as to smoothly interface with the capitulum of the humerus, said head having a peripheral surface which extends completely about said head, an undersurface that extends from said peripheral surface inward to said collar, and a concave proximal surface for contact with the capitulum, which concave surface is surrounded by a rim portion, said undersurface being substantially planar and aligned at an angle between about 95° and about 105° to said axis of rotation, a medial region of said head extending further in a distal direction than does a lateral region thereof so that said medial region of said head is substantially thicker than said lateral region of said head and said peripheral surface has a greater height in said medial region than in said lateral region, said collar being located between said undersurface and said stem and being aligned at an angle of between about 8° and about 22° to the axis of rotation of the radius in pronation-supination movement, and said collar being lesser in cross-sectional dimension than said head and being proportioned to be received within the annular ligament, so that said undersurface of said head circumscribes said collar providing a peripheral shoulder against which said annular ligament abuts.

8. An elbow prosthesis for insertion into a human elbow to replace the proximal end portion of the radius, which prosthesis comprises a one-piece body having an integral head, collar and stem, said stem being proportioned to be received within the medullary cavity of the radius, said head being shaped so as to smoothly interface with the capitulum of the humerus, said head having an outermost peripheral surface which extends completely about said head, an undersurface and a concave proximal surface for contact with the capitulum, which concave surface is surrounded by a rim, and said collar being located between said head and said stem and being lesser in cross-sectional dimension than said head with both said head and said collar being of generally circular cross-section and the radius of curvature of said collar being between about 70% and about 80% of the radius of curvature of said head, said collar being spaced from said outermost peripheral surface of said head so that said undersurface of said head circumscribes said collar providing a peripheral shoulder having the form of an annular surface region of decreasing diameter against which the annular ligament of the elbow articulates.

9. The elbow prosthesis of claim 8 wherein said head has a medial region which has a radius of curvature that is between about 5% and about 20% less than the curvature of the radial notch of the ulna against which it articulates.

10. The elbow prosthesis of claim 8 wherein said collar is symmetrical about its circumference and has an axial height between about 30% and about 40% of the total height of said head plus said collar.

11. The elbow prosthesis of of claim 8 wherein said stem is of polaygonal cross-section so as to be received within the medullary cavity of the radius and not rotate about its axis.

12. The elbow prosthesis of claim 8 wherein said collar has an axial height between about 20% and 40% of its diameter.

* * * * *